(12) United States Patent
Kolb

(10) Patent No.: US 11,083,553 B2
(45) Date of Patent: Aug. 10, 2021

(54) ORAL CARE DEVICE

(71) Applicant: Colgate-Palmolive Company, New York, NY (US)

(72) Inventor: Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 222 days.

(21) Appl. No.: 15/106,534

(22) PCT Filed: Dec. 19, 2013

(86) PCT No.: PCT/US2013/076564
§ 371 (c)(1),
(2) Date: Jun. 20, 2016

(87) PCT Pub. No.: WO2015/094284
PCT Pub. Date: Jun. 25, 2015

(65) Prior Publication Data
US 2016/0331500 A1    Nov. 17, 2016

(51) Int. Cl.
*A61C 19/06* (2006.01)
*A61K 8/02* (2006.01)
*A61Q 11/00* (2006.01)

(52) U.S. Cl.
CPC .......... *A61C 19/066* (2013.01); *A61K 8/0204* (2013.01); *A61Q 11/00* (2013.01)

(58) Field of Classification Search
CPC ..... A61C 19/066; A61K 8/0204; A61Q 11/00
See application file for complete search history.

(56) References Cited

U.S. PATENT DOCUMENTS

| | | | | |
|---|---|---|---|---|
| 6,129,929 A | * | 10/2000 | Wick | A61F 15/005 424/448 |
| 6,277,458 B1 | * | 8/2001 | Dirksing | C09J 7/02 428/40.1 |
| 2003/0168075 A1 | * | 9/2003 | Schwartz | A61C 3/06 132/309 |
| 2004/0005277 A1 | | 1/2004 | Willison et al. | |
| 2006/0292520 A1 | | 12/2006 | Dillon et al. | |
| 2009/0023106 A1 | | 1/2009 | Jacobs | |
| 2010/0304324 A1 | | 12/2010 | Dragan et al. | |
| 2012/0040307 A1 | * | 2/2012 | Postal | A61C 19/066 433/89 |

OTHER PUBLICATIONS

Corresponding Search Report for PCT/US2013/076564 dated Aug. 7, 2014.

* cited by examiner

Primary Examiner — Lezah Roberts

(57) ABSTRACT

Disclosed is an oral care device, comprising: an elongate strip having a major surface; and first and second tabs respectively extending from first and second portions of the major surface. Each of the first and second tabs is movable relative to the strip between a storage position and an operative position. The strip holds an oral care agent at the major surface of the strip. Also disclosed is a stack of the oral care devices located in an airtight package.

20 Claims, 1 Drawing Sheet

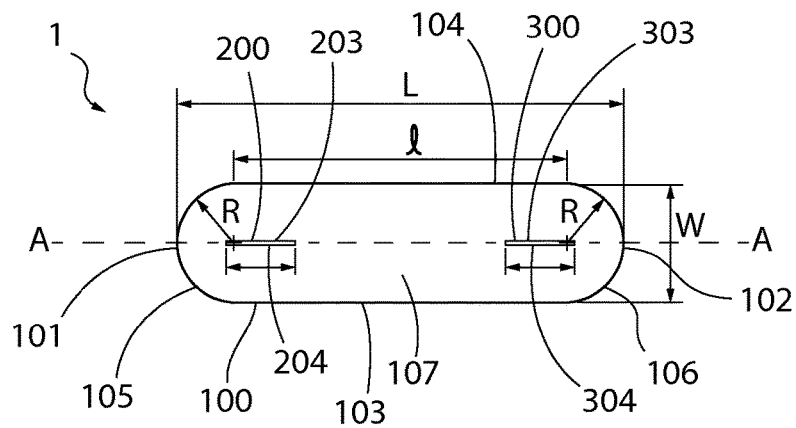
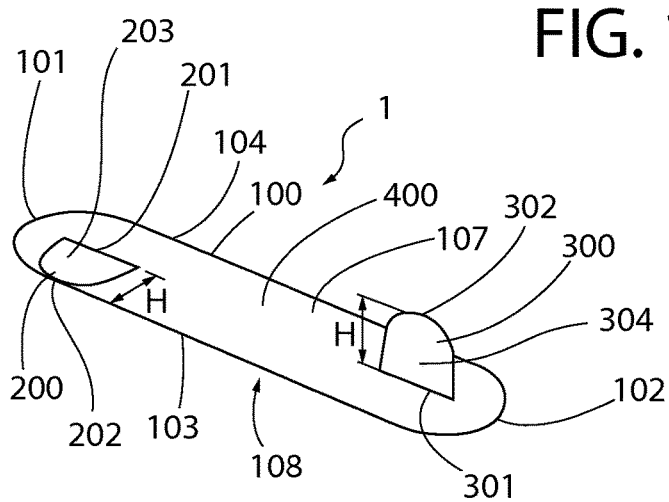
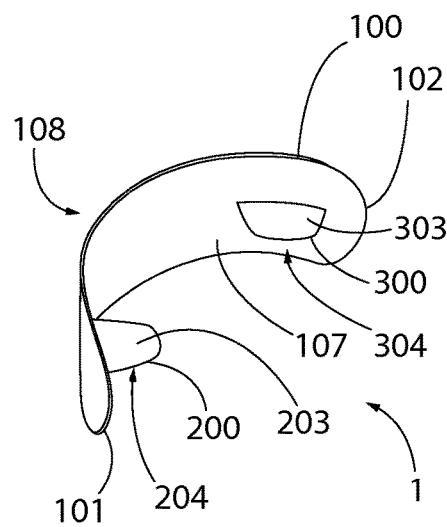
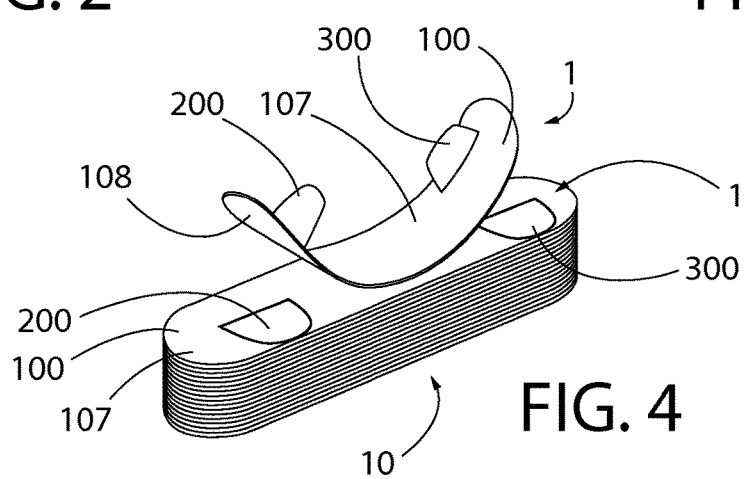

ORAL CARE DEVICE

CROSS-REFERENCE TO RELATED PATENT APPLICATIONS

The present application is a U.S. national stage application under 35 U.S.C. § 371 of PCT Application No. PCT/US2013/076564, filed Dec. 19, 2013, the entirety of which is incorporated by reference herein.

BACKGROUND

The present invention relates to an oral care device comprising a strip holding an oral care agent, such as a whitening agent.

It is known to provide an oral care agent, such as a whitening agent, in a tray or on a strip of material. In use, the tray or strip is placed in contact with a user's teeth or other surface in the oral cavity for a period of time to provide the oral care agent to the surface. These oral care agents are used for a wide variety of purposes, including the enhancement of hygiene and appearance, and the prevention or treatment of a variety of diseases and other oral cavity conditions in humans and in animals by delivering systemic or localized active agents. Conventional strips typically comprise a strip of material, such as a plastic film, with an oral care agent on one surface of the strip. Such strips can be difficult to retain in position in the oral cavity during use, and typically require adhesive for adhesion onto teeth. While conventional trays can be easier to retain in position in the oral cavity during use than conventional strips, they tend to be uncomfortable for the user to wear, require greater storage space than strips, and cost more to manufacture than strips.

There is a need for an oral care device that can be retained in position in the oral cavity during use without requiring the use of an adhesive. There also is a need for such an oral care device that is simpler and cheaper to manufacture, more comfortable to use, and more compact when not in use than conventional trays.

BRIEF SUMMARY

An embodiment of the present invention provides a first oral care device, comprising: an elongate strip having a major surface; and first and second tabs respectively extending from first and second portions of the major surface.

Optionally, each of the first and second tabs is movable relative to the strip between a storage position and an operative position.

Optionally, each of the first and second tabs is movable relative to the strip between the storage position and the operative position about an axis substantially parallel to a longitudinal axis of the strip.

Optionally, each of the first and second tabs is foldable relative to the strip between the storage position and the operative position.

Another embodiment of the present invention provides a second oral care device, comprising: an elongate strip having a major surface; and a first tab extending from a first portion of the major surface; wherein the first tab is movable relative to the strip between a storage position and an operative position.

Optionally, in the second oral care device, the first tab is movable relative to the strip between the storage position and the operative position about an axis substantially parallel to a longitudinal axis of the strip.

Optionally, in the second oral care device, the first tab is foldable relative to the strip between the storage position and the operative position.

Optionally, the second oral care device comprises a second tab extending from a second portion of the major surface, wherein the second tab is movable relative to the strip between a storage position and an operative position.

Optionally, in the second oral care device, the second tab is movable relative to the strip between the storage position and the operative position about an axis substantially parallel to a longitudinal axis of the strip.

Optionally, in the second oral care device, the second tab is foldable relative to the strip between the storage position and the operative position.

Optionally, in either of the first and second oral care devices, when the first tab is at the operative position, the first tab is substantially orthogonal to the first portion of major surface.

Optionally, in either of the first and second oral care devices, when the first tab is at the storage position, the first tab is substantially parallel to the first portion of the major surface.

Optionally, in either of the first and second oral care devices, when the second tab is at the operative position, the second tab is substantially orthogonal to the second portion of major surface.

Optionally, in either of the first and second oral care devices, when the second tab is at the storage position, the second tab is substantially parallel to the second portion of major surface.

Optionally, in either of the first and second oral care devices, the first and second tabs are spaced apart in an elongate direction of the strip. Further optionally, a distance between respective proximal ends of the first and second tabs in the elongate direction of the strip is equal to or greater than a quarter of a length of the strip in the elongate direction. Still further optionally, the distance between the respective proximal ends of the first and second tabs in the elongate direction of the strip is equal to or greater than a half of the length of the strip in the elongate direction.

Optionally, in either of the first and second oral care devices, the, or each, tab is substantially planar.

Optionally, in either of the first and second oral care devices, the strip has a length in the elongate direction of the strip, and a width perpendicular to the length and extending between first and second sides of the strip; and the, or each, tab has a proximal end fixed to the major surface at a position on the major surface away from each of the first and second sides of the strip. Further optionally, the proximal end of the, or each, tab is fixed to the major surface at a position on the major surface substantially halfway between the first and second sides of the strip.

Optionally, in either of the first and second oral care devices, the strip has a length in the elongate direction of the strip, and a width perpendicular to the length; the, or each, tab has a proximal end fixed to the major surface, a distal end, and a height between the proximal and distal ends; and the height is no more than half the width of the strip.

Optionally, in either of the first and second oral care devices, the strip is bendable.

Optionally, in either of the first and second oral care devices, the strip is transformable between a storage state, in which the major surface is substantially planar, and an operative state, in which the major surface is substantially concave.

Optionally, in either of the first and second oral care devices, the strip holds an oral care agent. Optionally, the oral care agent is at the major surface of the strip. Optionally the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

Another embodiment of the present invention provides a stack of oral care devices, wherein each of the oral care devices of the stack is one of the first and second oral care devices discussed above, optionally including any one or more of the above-described optional features of the first and second oral care devices discussed above.

Optionally, each of the oral care devices is one of the second oral care devices discussed above, and the first tab of each of the oral care devices is at the storage position relative to the strip of the oral care device. Each of the second oral care devices may include any one or more of the above-discussed optional features of the second oral care device.

Optionally, each of the oral care devices comprises a second tab extending from a second portion of the major surface, wherein the second tab is movable relative to the strip between a storage position and an operative position, and wherein the second tab of each of the oral care devices is at the storage position relative to the strip of the oral care device.

Optionally, the elongate strip of each of the oral care devices has a second major surface opposite from the major surface, and the oral care devices are stacked together with the major surface of one of the oral care devices of the stack facing the second major surface of an adjacent oral care device of the stack.

Optionally, the oral care devices of the stack are located in a package, optionally an airtight package. Optionally, the package may be a hollow toothbrush handle or a sealed package received within a hollow toothbrush handle.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 shows a front view of an oral care device according to an exemplary embodiment of the present invention, with a strip of the oral care device in its storage state and with first and second tabs of the oral care device at respective operative positions relative to the strip;

FIG. 2 shows a perspective view of the oral care device of FIG. 1, with the strip in its storage state, the first tab at its operative position relative to the strip and the second tab at its storage position relative to the strip;

FIG. 3 shows a perspective view of the oral care device of FIGS. 1 and 2, with the strip in its operative state and with the first and second tabs at their respective operative positions relative to the strip; and FIG. 4 shows a perspective view of a stack of oral care devices, each of the oral care devices being an oral care device as shown in FIGS. 1 to 3.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

FIGS. 1 to 3 illustrate an oral care device according to an exemplary embodiment of the present invention, generally designated with the reference numeral 1. The oral care device 1 generally comprises a strip 100 having first and second major surfaces 107, 108, and first and second tabs 200, 300 respectively extending from the first major surface 107.

With reference first to FIG. 1, the oral care device 1 is shown with the strip 100 in a storage state and with the first and second tabs 200, 300 at respective operative positions relative to the strip 100. The strip 100 of the oral care device 1 is rounded-oblong shaped. The strip 100 has a first end 101 and a second end 102 and is elongate between the first and second ends 101, 102. The strip 100 has a longitudinal axis (A-A) extending in the elongate direction of the strip 100, a length (L) in the elongate direction of the strip 100 and measured along the longitudinal axis (A-A) between the first and second ends 101, 102, and a width (W) perpendicular to the length and extending between first and second elongate sides 103, 104 of the strip 100. In the illustrated embodiment, the length (L) of the strip 100 is 75 millimeters and the width (W) of the strip 100 is 20 millimeters. In other embodiments, the length (L) of the strip 100 preferably is between 45 and 105 millimeters, and more preferably is between 55 and 95 millimeters.

Moreover, in other embodiments, the width (W) of the strip 100 preferably is between 10 and 30 millimeters, and more preferably is between 15 and 25 millimeters. The first and second ends 101, 102 lie on the longitudinal axis (A-A) and the first and second elongate sides 103, 104 are parallel to the longitudinal axis (A-A). In the illustrated embodiment, each of the first and second elongate sides 103, 104 has a length (l) that is less than the length (L) of the strip 100. Respective first ends of the first and second elongate sides 103, 104 are connected to the first end 101 of the strip 100 by a first curved end side 105, and respective second ends of the first and second elongate sides 103, 104 are connected to the second end 102 of the strip 100 by a second curved end side 106. Each of the first and second curved end sides 105, 106 is semi-circular with a diameter equal to the width (W) of the strip 100, and the points from which the radius (R) of each of the first and second curved end sides 105, 106 is measured lies on the longitudinal axis (A-A) of the strip 100. Accordingly, the first and second curved end sides 105, 106 transition smoothly into the first and second elongate sides 103, 104.

In variations to the illustrated embodiment, the radius (R) of the first and second curved end sides 105, 106 may be greater than half the width (W) of the strip 100, so that the first and second curved end sides 105, 106 do not transition smoothly into the first and second elongate sides 103, 104. In other variations to the illustrated embodiment, the strip 100 could have a different shape, such as a rectangular shape with the longitudinal axis (A-A) of the strip 100 parallel to the pair of longest sides of the rectangle.

The strip 100 is bendable so as to be transformable between the storage state as shown in FIGS. 1 and 2, in which the first major surface 107 is substantially planar, and an operative state as shown in FIG. 3, in which the first major surface 107 is concave. It is preferred that the strip 100 be more rigid than a conventional film whitening strip. In the illustrated embodiment, the strip 100 is resilient and tends to the storage state. However, in variations to the illustrated embodiment, the strip 100 may not be resilient, but may still be transformable between the storage and operative states. For example, the strip 100 may be malleable. In variations to the illustrated embodiment, the strip 100 may be substantially rigid and non-bendable, with the first major surface 107 being concave ready for use, so that the strip 100 is not transformable between operative and storage states.

The strip 100 holds an oral care agent 400. In the illustrated embodiment, the oral care agent 400 is at the first major surface 107 of the strip 100. More specifically, a majority, or all, of the first major surface 107 has the oral care agent 400 thereon. In the illustrated embodiment, the strip 100 is substantially non-porous and impermeable. In some embodiments of the invention, the first major surface 107 of the strip 100 is textured for holding the oral care agent 400. The first major surface 107 may include a plurality of dimples, cups or recesses, similar to the dimples on a golf ball, within which the oral care agent 400 is held. The oral care agent 400 may be held on the first major surface 107 through the provision of a specific relationship between a surface tension of the oral care agent and the dimensions of the dimples, cups or recesses. Other mechanisms by which the oral care agent 400 may be held on the first major surface 107 will be apparent to the skilled person in light of the full disclosure. The oral care agent may be sintered on the first major surface 107 and be activatable by a user's saliva. In variations to the illustrated embodiment, the oral care agent 400 additionally or alternatively is at the second major surface 108 of the strip 100, which is opposite from the first major surface 107. In further variations to the illustrated embodiment, the strip 100 may be porous or absorbent and the oral care agent 400 may be held in pores of the strip 100. In such variations, preferably the oral care agent 400 still is at the first major surface 107 of the strip 100 and/or at the second major surface 108 of the strip 100.

The oral care agent 400 may be in any form such as a solid or a flowable material including, without limitation, a fluid, a powder, a viscous pastes or gel, or a liquid. Any suitable oral care agent can be used in the present invention. For example, the oral care agent may be a whitening agent, including, without limitation, a peroxide containing tooth whitening composition. In the illustrated embodiment, the oral care agent is a whitening agent for whitening teeth. However, in variations to the illustrated embodiment, the oral care agent may be selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof The first and second tabs 200, 300 respectively extend from first and second portions of the first major surface 107 of the strip 100. Accordingly, when the strip 100 is transformed to its operative state, as shown in FIG. 3, the first and second tabs 200, 300 extend away from the concave first major surface 107. Each of the first and second tabs 200, 300 has a proximal end 201, 301 fixed to a respective portion of the first major surface 107 at a position on the first major surface 107 away from each of the first and second elongate sides 103, 104 of the strip 100. In the illustrated embodiment, each of the proximal ends 201, 301 of the tabs 200, 300 is fixed to a respective portion of the first major surface 107 at a position on the first major surface 107 substantially halfway between the first and second elongate sides 103, 104 of the strip 100. In other words, each of the proximal ends 201, 301 of the tabs 200, 300 lies on the longitudinal axis (A-A) of the strip 100. In variations to the illustrated embodiment, one or both of the proximal ends 201, 301 of the tabs 200, 300 may be fixed to a respective portion of the first major surface 107 at a different position on the first major surface 107 to that illustrated, such as between, or midway between, the longitudinal axis (A-A) of the strip 100 and one of the first and second elongate sides 103, 104 of the strip 100, or such as at, or adjacent, one of the first and second elongate sides 103, 104 of the strip 100. However, preferably, each of the proximal ends 201, 301 of the tabs 200, 300 is fixed to a respective portion of the first major surface 107 at a position on the first major surface 107 away from the first and second elongate sides 103, 104 of the strip 100, so that, in use, portions of the first major surface 107 between the longitudinal axis (A-A) and the respective first and second elongate sides 103, 104 of the strip 100 respectively contact the maxillary and mandibular teeth in a user's mouth, thereby preferably to apply the oral care agent simultaneously to the maxillary and mandibular teeth. In the illustrated embodiment, the distance between each of the proximal ends 201, 301 of the tabs 200, 300 and each of the first and second elongate sides 103, 104 in a direction perpendicular to the longitudinal axis (A-A) of the strip 100 is 10 millimeters. In variations to the illustrated embodiment, the distance between each of the proximal ends 201, 301 of the tabs 200, 300 and the first elongate side 103 in a direction perpendicular to the longitudinal axis (A-A) of the strip 100 is greater than the distance between each of the proximal ends 201, 301 of the tabs 200, 300 and the second elongate side 104 in a direction perpendicular to the longitudinal axis (A-A) of the strip 100. For example, the distance between each of the proximal ends 201, 301 of the tabs 200, 300 and the first elongate side 103 in a direction perpendicular to the longitudinal axis (A-A) of the strip 100 may be 12 millimeters, while the distance between each of the proximal ends 201, 301 of the tabs 200, 300 and the second elongate side 104 in a direction perpendicular to the longitudinal axis (A-A) of the strip 100 is 9 millimeters.

The proximal ends 201, 301 of the first and second tabs 200, 300 are spaced apart in the elongate direction of the strip 100. Indeed, the first and second tabs 200, 300 are spaced apart in the elongate direction of the strip 100. In the illustrated embodiment, a distance between the respective proximal ends 201, 301 of the first and second tabs 200 in the elongate direction of the strip 100 is greater than half of the length (L) of the strip 100 in the elongate direction. In variations to the illustrated embodiment, the distance between the respective proximal ends 201, 301 of the first and second tabs 200, 300 may be different to that illustrated, such as equal to or greater than a quarter of the length (L) of the strip 100 in the elongate direction, or equal to half of the length (L) of the strip 100 in the elongate direction. It is preferable that the first and second tabs 200, 300 be spaced apart sufficiently that the first and second tabs 200, 300 do not contact or interfere with each other when the strip 100 is bent to, or otherwise transformed into, its operate state. Moreover, it is preferable that the first and second tabs 200, 300 be spaced apart sufficiently that, when the oral care device 1 is in use, the first and second tabs 200, 300 are in contact with spaced-apart portions of the set of teeth of the user, so as to enable a user to anchor stably or retain stably the oral care device 1 in their mouth and relative to their teeth. For example, the first and second tabs 200, 300 may be spaced for respectively being trapped between left and right pairs of first or second maxillary and mandibular premolars or between left and right pairs of first or second maxillary and mandibular molars.

In the illustrated embodiment, each of the proximal ends 201, 301 of the first and second tabs 200, 300 has a length in the elongate direction of the strip 100 of 12 millimeters. In other embodiments, each of the proximal ends 201, 301 of the first and second tabs 200, 300 has a length in the elongate direction of the strip 100 that is preferably less than 20 millimeters, and more preferably is between 8 and 15 millimeters. It is preferable that the respective lengths of the proximal ends 201, 301 of the first and second tabs 200, 300 be long enough to provide sufficient anchoring of the first and second tabs 200, 300 to the strip 100, yet be short enough not to provide too great a resistance to the strip 100 being transformed from its storage state to its operative state. In the illustrated embodiment, the proximal ends 201, 301 of the first and second tabs 200, 300 are spaced from the first and second ends 101, 102 of the strip 100. The proximal end 201 of the first tab 200 is spaced from the first end 101 of the strip 100 along the longitudinal axis (A-A) of the strip 100 by 10 millimeters. Similarly, the proximal end 301 of the second tab 300 is spaced from the second end 102 of the strip 100 along the longitudinal axis (A-A) of the strip 100 by 10 millimeters. In other embodiments, the proximal end 201 of the first tab 200 is spaced from the first end 101 of the strip 100 along the longitudinal axis (A-A) of the strip 100 by a distance of preferably between 0 and 15 millimeters, more preferably between 0 and 10 millimeters, and the proximal end 301 of the second tab 300 is spaced from the second end 102 of the strip 100 along the longitudinal axis (A-A) of the strip 100 by a distance of preferably between 0 and 15 millimeters, more preferably between 0 and 10 millimeters. Accordingly, in some embodiments, the proximal end 201 of the first tab 200 is not spaced from the first end 101 of the strip 100 along the longitudinal axis (A-A) of the strip 100, and/or the proximal end 301 of the second tab 300 is not spaced from the second end 102 of the strip 100 along the longitudinal axis (A-A) of the strip 100.

Each of the first and second tabs 200, 300 is substantially planar with a first planar side 203, 303 and a second planar side 204, 304 opposite from the first planar side 203, 303. Each of the first and second tabs 200, 300 is movable relative to the strip 100 between a storage position, as shown for the first tab 200 only in FIG. 2, and an operative position, as shown for the second tab 300 only in FIG. 2. More specifically, in the illustrated embodiment, each of the first and second tabs 200, 300 is foldable relative to the strip 100 between the storage position and the operative position about an axis substantially parallel to the longitudinal axis (A-A) of the strip 100. When the first and second tabs 200, 300 are in their respective storage positions relative to the strip 100, the first and second tabs 200, 300 are substantially parallel to the first and second portions of the first major surface 107 from which they respectively extend. On the other hand, when the first and second tabs 200, 300 are in their respective operative positions relative to the strip 100, the first and second tabs 200, 300 are substantially orthogonal to the first and second portions of the first major surface 107 from which they respectively extend.

In variations to the illustrated embodiment, each of the first and second tabs 200, 300 is foldable relative to the strip 100 between the storage position and the operative position about an axis non-parallel to, such as substantially perpendicular to or at 45 degrees to, the longitudinal axis (A-A) of the strip 100. In some variations to the illustrated embodiment, the first and second tabs 200, 300 are not foldable relative to the strip 100 between the storage position and the operative position, but may be otherwise movable or rotatable relative to the strip 100 between the storage position and the operative position. For example, in some embodiments, the first and second tabs 200, 300 may be fixed to the strip 100 via respective hinges.

Each of the first and second tabs 200, 300 has a distal end 202, 302 distal from the first major surface 107, and a height (H) measured between the proximal 201, 301 and distal ends 202, 302 of the tab 200, 300. In the illustrated embodiment, the height (H) is equal to half the width (W) of the strip 100, i.e. the height (H) is 10 millimeters. Accordingly, in the illustrated embodiment and the preferred variations to the illustrated embodiment, when the first and second tabs 200, 300 are at their respective storage positions relative to the strip 100, no part of either of the first and second tabs 200, 300 lies outside of the area of the strip 100, which area is defined by the first and second elongate sides 103, 104 and the first and second curved end sides 105, 106 of the strip 100. In variations to the illustrated embodiment, the height (H) preferably is less than, but may be more than, half the width (W) of the strip 100. The height (H) preferably is between 5 and 20 millimeters, and more preferably is between 8 and 15 millimeters.

While in the illustrated embodiment the oral care device 1 comprises only two tabs 200, 300 extending from the first major surface 107 of the strip 100, in variations to the illustrated embodiment the oral care device 1 may comprise only one tab extending from the first major surface 107 of the strip 100. In such variations, the tab may be located substantially midway between the first and second ends 101, 102 of the strip 100. In such variations, the tab may be of considerably greater length in the elongate direction of the strip 100 to that of the first and second tabs 200, 300 of the illustrated embodiment. In other variations to the illustrated embodiment, the oral care device 1 may comprise more than two (e.g. three, four, five, or six) tabs respectively extending from respective portions of the first major surface 107.

In the illustrated embodiment, the first and second tabs 200, 300 are unitary with the strip 100. That is, the strip 100 and the first and second tabs 200, 300 are integrally formed. In variations to the illustrated embodiment, the first and second tabs 200, 300 may be formed separately from the strip 100 and may be fixed to the strip, e.g. by an adhesive or by welding. In the illustrated embodiment, each of the strip 100 and the first and second tabs 200, 300 is made from a plastic, such as a thermoplastic polymer, that is safe for oral use. In variations to this embodiment, the strip 100 and/or the first and second tabs 200, 300 may be made from a different material, such as card or cardboard.

According to an aspect of the present invention, there is provided a stack of a plurality of oral care devices, such as the stack 10 of oral care devices 1 shown in FIG. 4. Preferably, as is the case in the stack 10 of FIG. 4, the oral care devices 1 are stacked together with the first major surface 107 of one of the oral care devices 1 of the stack 10 facing the second major surface 108 of an adjacent oral care device 1 of the stack 10. In other words, preferably the oral care devices 1 are all orientated in the same direction in the stack 10. Also preferably, as is the case in the stack 10 of FIG. 4, the first and second tabs 200, 300 of each of the oral care devices 1 in the stack 10 is at its storage position relative to the strip 100 of the oral care device 1 from which it extends, and the strip 100 of each of the oral care devices 1 in the stack 10 is in its storage state, so that each of the oral care devices 1 in the stack 10, and indeed the stack 10 as a whole, is compact. Although not expressly shown in FIG. 4, preferably the oral care devices 1 of the stack 10 are located in a, preferably airtight, package, such as an openable box, thereby to preserve the oral care devices 1 and the oral care agent(s) thereof. In an embodiment, the package itself may be a hollow toothbrush handle (not shown) within which the oral care devices 1 may be received and stored. Alternatively, the package may be, for example, an openable box or resealable plastic enclosure which may be received and stored within a hollow toothbrush handle (not shown).

When a user wishes to use one of the oral care devices 1 of the stack 10, they open an opening of the package and preferably remove the oral care device 1 closest to the opening of the package. The user then moves the first and second tabs 200, 300 of the oral care device 1 from their respective storage positions to their respective operative positions, which in the illustrated embodiment is with the first and second tabs 200, 300 substantially orthogonal to the respective portions of the first major surface 107 from which they extend. The user then bends or otherwise transforms the strip 100 from its storage state to its operative state, and then inserts the oral care device 1 in their oral cavity with the first and second tabs 200, 300 facing their throat, the first major surface 107 facing the front, or outwardly-facing, surfaces of their teeth, and the second major surface 108 facing the inside of the lips. Given the thin nature of the strip 100, as measured between the first and second major surfaces 107, 108, the oral care device 1 is comfortable to wear during use. The user then moves their jaw upwards to trap the first and second tabs 200, 300 between some of their maxillary and mandibular teeth, thereby to retain the oral care device 1 in position relative to their teeth. The user then maintains this state for a predetermined time period, such as five, ten or fifteen minutes, to enable the oral care agent(s) held by the strip 100 to be held in contact with the surfaces of the user's teeth for a period sufficient to have a desired effect. In the present embodiment, the desired effect is whitening of the teeth, but in other embodiments the desired effect may additionally or alternatively be some other effect. Once the predetermined time period has expired, the user removes the oral care device 1 from their mouth. It is intended that the oral care device 1 be used only once to apply the oral care agent to an oral surface. Preferably, the oral care device 1 is made of recyclable materials, such as a plastic or cardboard, and the oral care device 1 may be recycled after use.

Accordingly, the oral care device 1 is easier to retain in position in the oral cavity during use than conventional oral care strips, without requiring the use of an adhesive, yet it is simpler and cheaper to manufacture, more comfortable to use, and more compact to store than conventional oral care trays.

While in each of the above-described embodiments the strip 100 of the oral care device 1 holds the oral care agent 400, in respective variations to those embodiments, neither the strip 100 nor any other part of the oral care device 1 may hold an oral care agent, so that the oral care device 1 is free of oral care agent. The oral care agent may be provided or stored separately from the oral care device 1, or from the stack 10 of oral care devices 1, and it may be intended that the oral care agent(s) be applied by a user to the first major surface 107 of the strip 100 immediately prior to use.

What is claimed is:

1. An oral care device, comprising:
an elongate strip comprising:
   a major surface bounded by a perimeter edge;
   a longitudinal axis extending from a first side of the perimeter edge to a second side of the perimeter edge, the first and second sides of the perimeter edge being opposite one another;
   a transverse axis extending perpendicular to the longitudinal axis from a third side of the perimeter edge to a fourth side of the perimeter edge, the third and fourth sides of the perimeter edge being opposite one another;
   a length measured along the longitudinal axis from the first side of the perimeter edge to the second side of the perimeter edge; and
   a width measured along the transverse axis from the third side of the perimeter edge to the fourth side of the perimeter edge, the length being greater than the width; and
a first tab extending from the major surface of the elongate strip, the first tab having a proximal end fixed to the major surface and a distal end, the first tab foldable at the proximal end of the first tab along a first fold axis that is substantially coaxial with the longitudinal axis and spaced from each of the third and fourth edges between: (1) a storage position in which a surface of the first tab overlies and contacts the major surface of the elongate strip; and (2) an operative position in which the first tab protrudes from the major surface of the elongate strip and the surface of the first tab is no longer in contact with the major surface;
a second tab extending from the major surface of the elongate strip, the second tab having a proximal end fixed to the major surface and a distal end, the second tab foldable at the proximal end of the second tab along a second fold axis that is substantially coaxial with the longitudinal axis and spaced from each of the third and fourth edges between: (1) a storage position in which a surface of the second tab overlies and contacts the major surface of the elongate strip; and (2) an operative position in which the second tab protrudes from the major surface of the elongate strip and the surface of the second tab is no longer in contact with the major surface;
the first and second tabs spaced from one another and located on opposite sides of the transverse axis of the elongate strip;
wherein when both of the first and second tabs are in the operative positions, the major surface comprises a maxillary tooth contact region above the proximal ends of the first and second tabs and a mandibular tooth contact region below the proximal ends of the first and second tabs.

2. An oral care device, comprising:
an elongate strip comprising:
   a major surface bounded by a perimeter edge;

a longitudinal axis extending from a first side of the perimeter edge to a second side of the perimeter edge, the first and second sides of the perimeter edge being opposite one another;
a transverse axis extending perpendicular to the longitudinal axis from a third side of the perimeter edge to a fourth side of the perimeter edge, the third and fourth sides of the perimeter edge being opposite one another;
a length measured along the longitudinal axis from the first side of the perimeter edge to the second side of the perimeter edge; and
a width measured along the transverse axis from the third side of the perimeter edge to the fourth side of the perimeter edge; and
a first tab extending from the major surface of the elongate strip, the first tab having a proximal end fixed to the major surface and a distal end, the first tab foldable at the proximal end of the first tab along a first fold axis that is substantially coaxial with the longitudinal axis and spaced from each of the third and fourth edges between: (1) a storage position in which a surface of the first tab overlies and contacts the major surface of the elongate strip; and (2) an operative position in which the first tab protrudes from the major surface of the elongate strip and the surface of the second tab is no longer in contact with the major surface;
wherein when the first tab is in the operative position, the major surface comprises a maxillary tooth contact region above the proximal end of the first tab and a mandibular tooth contact region below the proximal end of the first tab.

3. The oral care device of claim 2, wherein the proximal end of the first tab is fixed to the major surface at a position on the major surface substantially halfway between the third and fourth sides of the perimeter edge.

4. The oral care device of claim 2, wherein, when the first and second tabs are in the storage position, no portion of the first and second tabs protrude beyond the perimeter edge of the major surface of the elongate strip.

5. The oral care device of claim 1, wherein, when the first tab is at the operative position, the first tab is substantially orthogonal to the first portion of major surface; and wherein, when the first tab is at the storage position, the first tab is substantially parallel to the first portion of the major surface.

6. The oral care device of claim 5, wherein, when the second tab is at the operative position, the second tab is substantially orthogonal to the second portion of major surface; and wherein, when the second tab is at the storage position, the second tab is substantially parallel to the second portion of major surface.

7. The oral care device of claim 6, wherein a distance between respective proximal ends of the first and second tabs along the longitudinal axis is equal to or greater than a quarter of the length of the strip.

8. The oral care device of claim 1, wherein each of the first and second tabs is substantially planar.

9. The oral care device of claim 1, wherein the proximal end of each tab is fixed to the major surface at a position on the major surface substantially halfway between the third and fourth sides of the perimeter edge.

10. The oral care device of claim 2, wherein the first tab has a height between the proximal and distal ends; and
wherein the height is no more than half the width of the strip.

11. The oral care device of claim 1, wherein the strip is transformable between a storage state, in which the major surface is substantially planar, and an operative state, in which the major surface is substantially concave.

12. The oral care device of claim 1, wherein the strip holds an oral care agent on the major surface of the strip.

13. The oral care device of claim 12, wherein the oral care agent is selected from the group consisting of: antibacterial agents; oxidative or whitening agents;
enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof.

14. A stack of oral care devices, wherein each of the oral care devices of the stack is as defined in claim 1.

15. The stack of oral care devices of claim 14, wherein each of the first and second tabs is movable relative to the strip between a storage position and an operative position, and wherein the first tab of each of the oral care devices is at the storage position relative to the strip of the oral care device, wherein each of the first and second tabs is movable relative to the strip between a storage position and an operative position, and wherein the second tab of each of the oral care devices is at the storage position relative to the strip of the oral care device.

16. The stack of oral care devices of claim 14, wherein the elongate strip of each of the oral care devices has a second major surface opposite from the major surface, and
wherein the oral care devices are stacked together with the major surface of one of the oral care devices of the stack facing the second major surface of an adjacent oral care device of the stack.

17. An oral care device, comprising:
an elongate strip comprising:
a major surface bounded by a perimeter edge;
a longitudinal axis extending from a first side of the perimeter edge to a second side of the perimeter edge, the first and second sides of the perimeter edge being opposite one another;
a transverse axis extending perpendicular to the longitudinal axis from a third side of the perimeter edge to a fourth side of the perimeter edge, the third and fourth sides of the perimeter edge being opposite one another;
a length measured along the longitudinal axis from the first side of the perimeter edge to the second side of the perimeter edge; and
a width measured along the transverse axis from the third side of the perimeter edge to the fourth side of the perimeter edge; and
a first tab extending from the major surface of the elongate strip, the first tab having a proximal end fixed to the major surface and a distal end, the first tab foldable at the proximal end of the first tab along a first fold axis that is substantially coaxial with the longitudinal axis and spaced from each of the third and fourth edges between: (1) a storage position in which a surface of the first tab overlies and contacts the major surface of the elongate strip; and (2) an operative position in which the first tab protrudes from the major surface of the elongate strip and the surface of the first tab is no longer in contact with the major surface; and a second tab extending from the major surface of the elongate strip, the second tab having a proximal end fixed to the major surface and a distal end, the second tab foldable at the proximal end of the second tab along a second fold axis that is substantially coaxial with the longitudinal axis and spaced from each of the third and fourth edges between: (1) a storage position in which a surface of the second tab overlies and contacts the major surface of the elongate strip; and (2) an operative position in which the second tab protrudes from the major surface of the elongate strip and the surface of the second tab is no longer in contact with the major surface;

wherein, when the first and second tabs are in the storage position, no portion of the first and second tabs protrude beyond the perimeter edge of the major surface of the elongate strip.

18. The oral care device of claim 1, wherein, when the first and second tabs are in the storage position, each the first and second tabs are contained within the perimeter edge of the major surface of the elongate strip.

19. The oral care device of claim 1, wherein, when the first and second tabs are in the storage position, no portion of the first and second tabs protrude beyond the perimeter edge of the major surface of the elongate strip.

20. The oral care device of claim 1, wherein, when the first and second tabs are in the storage position, an entirety of the surfaces of each of the first and second tabs is in contact with the major surface of the elongate strip.

* * * * *